United States Patent [19]

Vorbrueggen et al.

[11] Patent Number: 5,162,353
[45] Date of Patent: Nov. 10, 1992

[54] CARBACYCLINS, PROCESSES FOR THEIR PREPARATION, AND THEIR USE AS MEDICINAL AGENTS

[75] Inventors: Helmut Vorbrueggen; Bob Nieuweboer; Claus-Steffen Stuerzebecher, all of Berlin, Fed. Rep. of Germany

[73] Assignee: Schering Aktiengesellschaft, Berlin and Bergkamen, Fed. Rep. of Germany

[21] Appl. No.: 570,446

[22] Filed: Aug. 21, 1990

Related U.S. Application Data

[60] Division of Ser. No. 164,758, Mar. 7, 1988, Pat. No. 4,971,987, which is a continuation of Ser. No. 864,345, filed as PCT/DE85/00246, Jul. 18, 1985, abandoned, and a continuation of Ser. No. 89,364, Aug. 31, 1987, abandoned.

[30] Foreign Application Priority Data

Jul. 27, 1984 [DE] Fed. Rep. of Germany ....... 3428266
Nov. 29, 1985 [DE] Fed. Rep. of Germany ....... 3542745

[51] Int. Cl.⁵ .................. C07C 177/00; A61K 31/557
[52] U.S. Cl. .................... 514/374; 514/452; 514/530; 514/561; 514/567; 514/564; 514/573; 514/657; 514/659; 514/681; 514/691; 548/237; 548/238; 549/373; 549/374; 549/415; 560/39; 560/56; 560/116; 560/119; 562/444; 562/466; 562/498; 562/501
[58] Field of Search ............... 560/119, 39, 56, 116; 562/501, 444, 466, 498; 514/374, 452, 530, 561, 567, 569, 573, 657, 659, 681, 691; 548/237, 238; 549/373, 374, 415; 564/98, 443, 454; 568/64, 374

[56] References Cited

U.S. PATENT DOCUMENTS 4,487,961 12/1984 Aristoff .................. 562/501

Primary Examiner—Robert Gerstl
Attorney, Agent, or Firm—Millen, White, Zelano and Branigan

[57] ABSTRACT

The invention relates to carbacyclin derivatives with general formula I:

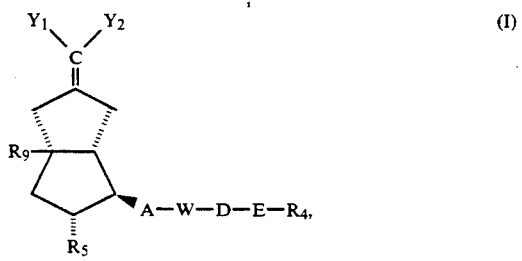

in which $Y_1$ stands for the radical $-CH_2-X-(CH_2)_n-R_1$ or the radical

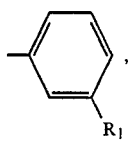

n, 1 or 3,
$R_1$, the radical

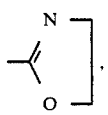

the radical

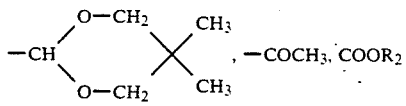

$R_9$ stands for the radical $-(CH_2)_m-R_6$ or the radical $-(CH_2)_{m-o}-[Z_1-(CH_2)_{m-p}]_x-[Z_2-(CH_2)_{m-q}]_y-R_6$,
m=2-20,
o, p, and q are less than or equal to 19,
x, y=0, 1 or 2,
$Z_1$ stands for a cis—CH=CH group, a trans—CH=CH group of a —C≡C group, and each of these groups must be separated at least by a methylene group from the C-9 carbon atom of the carbacyclin bicyclic compound,
$Z_2$ stands for oxygen, sulfur, an NH or an N methyl group,
$R_6$ stands for amino, methylamino, hydroxy, carboxy or mercapto,
X an oxygen atom or a methylene group,
$Y_2$ hydrogen or fluorine,
A a $-CH_2-CH_2$, trans—CH=CH or —C≡C group,
W a free or functionally modified hydroxy methylene group,
D a straight-chain, saturated alkylene group with 1-5 C atoms,
E stands for a direct bond, a —C≡C group or a —CH=CR_7 group,
$R_4$ stands for an alkyl group with 1-10 C atoms,
$R_5$ stands for a free or functionally modified hydroxy group.

The invention also relates to carbacyclin derivatives of general Formula I'

(Abstract continued on next page.)

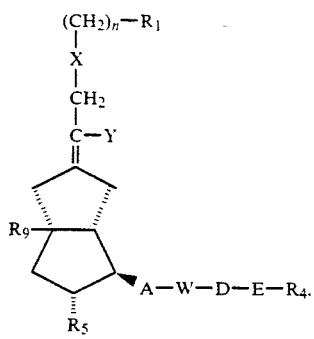

wherein
n is 1 or 3
R₁ is the residue

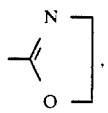

the residue

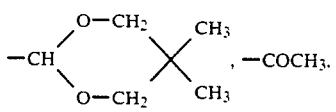

the residue $COOR_2$ wherein $R_2$ can mean hydrogen or alkyl of 1-10 carbon atoms optionally substituted by halogen, phenyl, $C_1$-$C_4$-alkoxy or $C_1$-$C_4$-dialkylamino; cycloalkyl, aryl, or a heterocyclic residue, or is the residue $CONHR_3$ with $R_3$ meaning hydrogen or an alkanoyl or alkanesulfonyl residue of respectively 1-10 carbon atoms, $R_9$ is an alkyl group of 1-10 carbon atoms or the group $-C\equiv C-(CH_2)_m-R_6$ wherein m is 1 to 16 and $R_6$ is hydrogen, hydroxy, amino or trimethylsilyl, X is an oxygen atom or, if $R_9$ means an alkyl group of 5-10 carbon atoms, a methylene group, and Y is hydrogen or fluorine, to processes for their preparation, and to medicinal agents containing these compounds.

12 Claims, No Drawings

CARBACYCLINS, PROCESSES FOR THEIR PREPARATION, AND THEIR USE AS MEDICINAL AGENTS

CROSS-REFERENCE TO RELATED APPLICATIONS

This is a division of application Ser. No. 07/164,758 of Mar. 7, 1988, now U.S. Pat. No. 4,871,987 which is a continuation application of U.S. Ser. No. 864,345, filed on May 12, 1986, now abandoned which is derived from International Application No. PCT/DE85/00246, filed on Jul. 18, 1985, and also is a continuation application of U.S. Ser. No. 089,364, filed on Aug. 31, 1987, now abandoned which is derived from International Application No. PCT/DE86/00484 which was filed on Nov. 28, 1986. The entire disclosures of the parent applications are hereby incorporated by reference.

The invention relates to new carbacyclin derivatives, process for their production and their use as a drug. In U.S. Pat. No. 4,420,632, 9-alkylated carbacyclin derivatives are described which have antithrombotic, antisecretory and bronchodilating qualities. In addition, they act to inhibit platelet aggregations.

It was found that carbacyclin analogues, chain lengthened in the 9 position, with a reactive group in omega-position can be bonded to polymer carriers with only a small loss of biological activity The compounds according to the invention are suitable for the inhibition of platelet aggregations, blood pressure reduction by vasodilation, inhibition of stomach acid secretion and for the preparation of antibodies to carbacyclins after chemical bonding with proteins.

The invention relates to carbacyclin derivatives with general formula I:

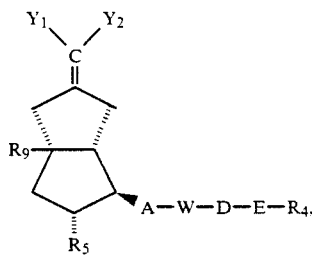

(I)

in which
$Y_1$ stands for the radical $-CH_2-X-(CH_2)_n-R_1$ or the radical

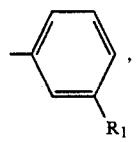, n, 1 or 3,
$R_1$, the radical

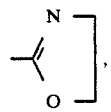, the radical

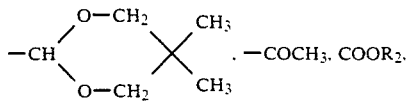

and $R_2$ can stand for hydrogen or optionally alkyl with 1-10 C atoms substituted with halogen, phenyl, $C_1$-$C_4$ alkoxy or $C_1$-$C_4$ dialkyl amino; cycloalkyl, aryl or a heterocyclic radical, or the radical $CONHR_3$, with $R_3$ standing for hydrogen or an alkanoyl or alkane sulfonyl radical each with 1-10 C atoms, $R_9$ stands for the radical $-(CH_2)_m-R_6$ or the radical $-(CH_2)_{m-o}-[Z_1-(CH_2)_{m-p}]_x-[Z_2-(CH_2)_{m-q}]_y-R_6$, $m = 2$-$20$, o, p, and q are less than or equal to 19, x, y = 0, 1 or 2, $Z_1$ stands for a cis—$CH=CH$ group, a trans—$CH=CH$ group or a —$C\equiv C$ group, and each of these groups must be separated at least by a methylene group from the C-9 carbon atom of the carbacyclin bicyclic compound, $Z_2$ stands for oxygen, sulfur, an NH or an N methyl group, $R_6$ stands for amino, methylamino, hydroxy, carboxy or mercapto, X an oxygen atom or a methylene group, $Y_2$ hydrogen or fluorine, A a —$CH_2-CH_2$, trans—$CH=CH$ or —$C\equiv C$ group, W a free or functionally modified hydroxy methylene group or a free or functionally modified

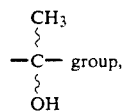 group, and the OH group can be in alpha or beta position,
D stands for the group

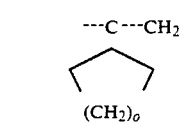

a straight-chain, saturated alkylene group with 1-5 C atoms, a branched, saturated or a straight chain or branched unsaturated alkylene group with 2-5 C atoms, which optionally can be substituted with fluorine atoms, o is 1, 2, or 3, E stands for a direct bond, a —$C\equiv C$ group or a —$CH=CR_7$ group and $R_7$ stands for a hydrogen atom, an alkyl group with 1-5 C atoms or halogen, $R_4$ stands for an alkyl group with 1-10 C atoms, a cycloalkyl group with 3-10 C atoms or an aryl group optionally substituted with 6-10 C atoms, or a heterocyclic group, $R_5$ stands for a free or functionally modified hydroxy group and, if $R_2$ represents a hydrogen atom, whose salts have physiologically well-tolerated bases.

As alkyl groups $R_2$, straight- or branched-chain alkyl groups with 1-10 C atoms are suitable, such as methyl, ethyl, propyl, isopropyl, butyl, isobutyl, tert-butyl, pentyl, isopentyl, neopentyl, heptyl, hexyl, decyl.

The alkyl groups $R_2$ can optionally be substituted once or several times with halogen atoms, $C_1-C_4$ alkoxy groups, phenyl and di-$C_1-C_4$ alkylamines. Easily substituted alkyl groups are preferred.

As substituents there can be mentioned, for example, fluorine, chlorine or bromine atoms, phenyl, dimethylamino, diethylamino, methoxy, ethoxy.

As preferred alkyl groups $R_2$, there can be mentioned those with 1-4 C atoms, such as methyl, ethyl, propyl, dimethylaminopropyl, isobutyl, butyl.

As aryl groups $R_2$, both substituted and unsubstituted aryl groups are suitable, such as phenyl, 1-naphtyl and 2-naphtyl, which can each be substituted with 1-3 halogen atoms, a phenyl group, 1-3 alkyl groups each with 1-4 C atoms, a chloromethyl, fluoromethyl, trifluoromethyl, carboxyl, hydroxy or alkoxy group with 1-4 C atoms.

Preferred are substituents in the 3 and 4 position on the phenyl ring, for example with fluorine, chlorine, alkoxy or trifluoromethyl or with hydroxy in the 4 position The cycloalkyl group $R_2$ can contain 4-10 preferably 5 and 6 carbon atoms in the ring. The rings can be substituted with alkyl groups with 1-4 carbon atoms. For example, there can be mentioned cyclopentyl, cyclohexyl, methylcyclohexyl and adamantyl.

As heterocyclic groups $R_2$, 5- and 6-member heterocyclic compounds containing at least 1 heteroatom, preferably nitrogen, oxygen or sulfur, are suitable. For example, there can be mentioned 2-furyl, 3-furyl, 2-thienyl, 3-thienyl, 2-pyridyl, 3-pyridyl, 4-pyridyl, etc.

As the acid radical $R_3$, physiologically well-tolerated acid radicals are suitable. Preferred acids are organic carboxylic acids and sulfonic acids with 10-10 C atoms which belong to the aliphatic, cycloaliphatic, aromatic, aromatic-aliphatic and heterocyclic series. These acids can be saturated, unsaturated and/or polybasic and/or substituted in the usual way. As examples of the substituents there can be mentioned $C_1-C_4$-alkyl, hydroxy, $C_1-C_4$ alkoxy, oxo or amino groups or halogen atoms (F, Cl, Br).

For example, there can be mentioned the following carboxylic acids: formic acid, acetic acid, propionic acid, butyric acid, isobutyric acid, valeric acid, isovaleric acid, caproic acid, heptanoic acid, caprylic acid, nonanoic acid, capric acid, undecylenic acid, lauric acid, tridecylenic acid, myristic acid, pentadecylenic acid, trimethylacetic acid, diethylacetic acid, tert-butyl acetic acid, cyclopropyl acetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted with halogen, trifluoromethyl, hydroxy, alkoxy or carboxyl groups, nicotinic acid, isonicotinic acid, 2-furancarboxylic acid, cyclopentylpropionic acid. Acyl radicals with up to 4 carbon atoms are considered as especially preferred. As sulfonic acids, methanesulfonic acid, ethanesulfonic acid, isopropanesulfonic acid, beta-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis-(beta-chloroethyl)-aminosulfonic acid, N,N-diisobutylaminosulfonic acid, N,N-dibutylaminosulfonic acid, pyrrolidino-, piperidino-, piperazino-, N-methylpiperazino- and morpholine-sulfonic acid are suitable, and sulfonic acids with up to 4 C atoms are especially preferred.

The hydroxy groups $R_5$ and in W can be functionally modified, for example by etherification or esterification, and the free or modified hydroxy groups in W can be in the alpha or beta position, free hydroxy groups being preferred.

As ether and acyl radicals, the radicals known to a man of the art are suitable. Preferred are easily cleavable ether radicals such as the tetrahydropyranyl, tetrahydrofuranyl, alpha-ethoxyethyl, trimethylsilyl, dimethyl-tert butyl-silyl and tri-p-benzyl silyl radical. As acyl radicals, the same as mentioned for $R_3$ are suitable; for example there can be mentioned acetyl, propionyl, butyryl, benzoyl.

As alkyl groups $R_4$, straight and branched-chain, saturated and unsaturated alkyl radicals, preferably saturated and with 1-10, especially 1-4 C atoms, are suitable.

For example there can be mentioned methyl, ethyl, propyl, butyl, isobutyl, tert-butyl, pentyl, hexyl, heptyl, octyl, butenyl, isobutenyl, propenyl, pentenyl, hexenyl.

The cycloalkyl group $R_4$ can contain 3-10, preferably 5 and 6 carbon atoms in the ring. The rings can be substituted with alkyl groups with 1-4 carbon atoms. For example, there can be mentioned cyclopentyl, cyclohexyl, methylcyclohexyl and adamantyl.

As substituted or unsubstituted aryl groups $R_4$ the following are suitable, for example: phenyl, 1-naphthyl and 2-naphthyl, which can each be substituted with 1-3 halogen atoms, a phenyl group, 1-3 alkyl groups each with 1-4 C atoms, a chloromethyl, fluoromethyl, trifluoromethyl, carboxyl, $C_1-C_4$ alkoxy or hydroxy group. Substitution in the 3 and 4 position on the phenyl ring is preferred, for example with fluorine, chlorine, $C_1-C_4$ alkoxy or trifluoromethyl or in the 4 position with hydroxy.

As heterocyclic groups $R_4$, 5- and 6-member heterocyclic compounds which contain at least 1 heteroatom, preferably nitrogen, oxygen or sulfur, are suitable. For example, there can be mentioned 2-furyl, 2-thienyl, 2-pyridyl, 3-pyridyl, 4-pyridyl, 3-furyl, 3-thienyl, among others.

As alkylene group D, straight-chain or branched-chain, saturated and unsaturated alkylene radicals, preferably saturated with up to 5 C atoms, are suitable, which can optionally be substituted with fluorine atoms, 1,2-methylene, 1,1-trimethylene, 1,1-tetramethylene or 1,1-pentamethylene. Examples are: methylene, fluoromethylene, ethylene, 1,2 propylene, ethylethylene, trimethylene, tetramethylene, pentamethylene, 1-methyltetramethylene, 1-methyl trimethylene, 1,1-trimethylene ethylene, 1,1-tetramethylene ethylene.

Especially preferred compounds of this invention are those with E as —C≡C— or —CH=CR$_7$, where $R_7$ represents an alkyl group with 1-5 C atoms.

As the alkyl group $R_7$ with 1-5 C atoms, the groups just named for the alkyl group $R_4$ are suitable.

With $R_7$ as halogen, fluorine, chlorine and bromine are meant.

For $R_9$ as —(CH$_2$)$_m$—R$_6$, alkylene groups with 2 to 20 C atoms are suitable, which can still contain one or more groups $Z_1$ or $Z_2$ such as —(CH$_2$)$_{m\text{-}o}$—[Z$_1$—(CH$_2$)$_{m\text{-}p}$]$_x$—[Z$_2$—CH$_2$)$_{m\text{-}q}$]$_y$—R$_6$, where m=2-20 and o, p, and q together are 16, such as, —(CH$_2$)$_5$—NH$_2$, —(CH$_2$)$_6$—NHCH$_3$, —(CH$_2$)$_2$—O—(CH$_2$)$_2$—COOH, —(CH$_2$)$_2$—O—(CH$_2$)$_3$—NH$_2$, —(CH$_2$)$_3$—O—(CH$_2$)$_3$—NH$_2$, —(CH$_2$)$_2$—O—(CH$_2$)$_2$—O—(CH$_2$)$_2$—OH,

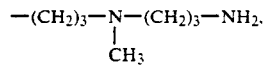

—CH$_2$—C=C—(CH$_2$)$_2$—NH$_2$, —(CH$_2$)$_2$—C=C—(CH$_2$)$_2$—NH$_2$, —(CH$_2$)$_2$—C≡C—(CH$_2$)$_2$—O—(CH$_2$)$_2$—SH, etc.

For salt formation with the free acids (R$_2$=H), inorganic and organic bases are suitable, such as they are known to a man of the art for the formation of physiologically well tolerated salts. For example, there can be mentioned alkali hydroxides such as sodium and potassium hydroxide, alkaline-earth hydroxides such as calcium hydroxide, ammonia, amines such as ethanolamine, diethanolamine, triethanolamine, N-methylglucamine, morpholine, tris-(hydroxymethyl)methylamine, etc.

The invention relates further to processes for the production of carbacyclins of general formula I according to the invention, characterized in that a) a compound of general formula IV

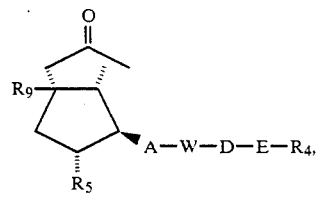

in which A, W, D, E, R$_4$, R$_5$ and R$_9$ have the meanings already given, and with a Wittig reagent of general formula V and VI or a dianion of the formula VII

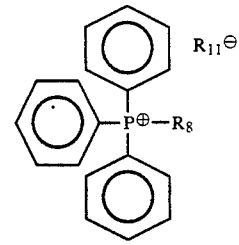

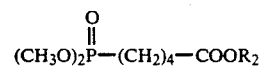

(VI)

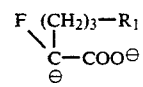

(VII)

in which R$_2$ has the meaning already given and R$_8$ stands for the radicals

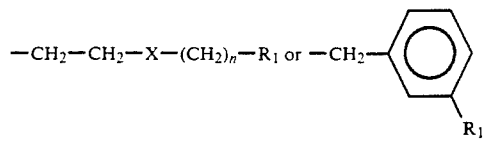

with the meanings already mentioned for X, n and R$_1$ and R$_{11}$ stand for bromine or chlorine, is reacted in the presence of K-tert-butylate or b) a compound of general formula VIII, which is obtained from the corresponding 4-ester by DIBAH reduction

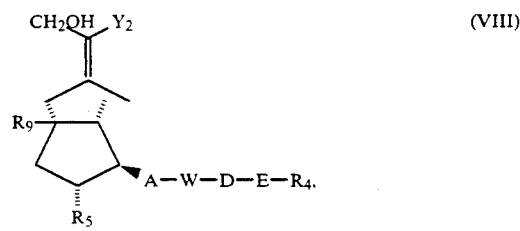

in which A, W, D, E, R$_4$, R$_5$, R$_9$, and Y$_2$ have the meanings already given, optionally after protection of present free hydroxy or amino groups with a haloalkane acid derivative of general formula IX

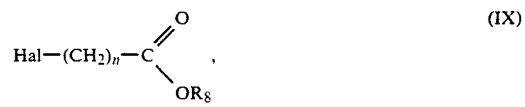

in which n is 1 or 3, Hal is a chlorine or bromine atom and R$_8$ is an alkyl radical with 1–4 C atoms or an alkaline metal, is etherified in the presence of a base and, optionally, isomers are then separated in any order and/or protected hydroxy groups are released and/or free hydroxy groups esterified, etherified and/or a free carboxyl group esterified and/or an esterified carboxyl group saponified or a carboxyl group converted into an amide or with a physiologically well tolerated base into a salt.

The reaction of the compound of general formula VIII with a haloalkane acid derivative of general formula IX is performed at temperatures of 0° C. to 100° C., preferably 10° to 80° C., in an aprotic solvent or solvent mixture, for example dimethyl sulfoxide, dimethylformamide, tetrahydrofuran, etc. As bases, the bases known to a man of the art for etherifications are suitable, such as sodium hydride, potassium tert-butylate, butyllithium, etc.

The starting compounds of formula IV are obtained by the reaction of compounds of formula II

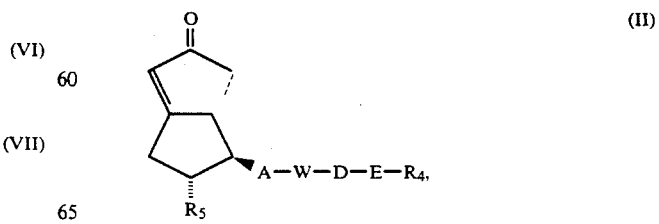

with Grignard reagents of formula III

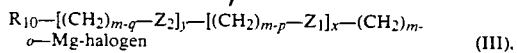

$$R_{10}-[(CH_2)_{m \cdot q}-Z_2]_y-[(CH_2)_{m \cdot p}-Z_1]_x-(CH_2)_{m \cdot o}-Mg\text{-halogen} \qquad (III).$$

in which $R_4$, $R_5$, A, W, D, E, $Z_1$, $Z_2$, m, o, p, q have the indicated meanings, in the presence of copper(II) salts and by subsequent introduction of the upper side chain by Wittig reaction of the 5-ring carbonyl group and conversion of the group $R_{10}$ into the group $R_6$. For the group $R_{10}$, amino groups protected by, for example, 1,1,4,4-tetramethyl-1,4-dichlorodisilylethane or by phthalic anhydride or by other typical amino groups protected by amino protection groups, and by hydroxy groups protected by tert-butyldiphenylsilyl or THP groups and by conversion into orthoesters or oxazoline-protected carboxyl groups.

After cleavage of the protection groups from nitrogen or after chemical conversion of the hydroxy or amide groups into amino groups, the desired substituents $R_6=NH_2$ are obtained. For this conversion of a hydroxy group into an amino group, the Mitsunobu reaction (see Synthesis 1, 1981) or the reduction of the azide to amine can be used.

The saponification of the carbacyclin ester is performed according to methods known to a man of the art, for example with basic catalysts.

The introduction of the ester group $COOR_2$ for $R_1$, in which $R_2$ represents an alkyl group with 1–10 C atoms, occurs according to methods known to a man of the art. The carboxyl compounds are reacted, for example, with diazohydrocarbons in a way known in the art. Esterification with diazohydrocarbons occurs, for example, by mixing a solution of diazohydrocarbon in an inert solvent, preferably in diethyl ether with the carboxyl compound in the same or in another inert solvent, for example, methylene chloride. After the reaction is finished in 1 to 30 minutes, the solvent is removed and the ester is purified in the usual way. Diazoalkanes are either known or can be produced by known methods (Org. Reactions Vol. 8, pages 389–394 (1954)).

The introduction of the ester group $COOR_2$ for $R_1$, in which $R_2$ represents a substituted or unsubstituted aryl group, occurs according to methods known to a man of the art. For example, the carboxyl compounds are reacted with the corresponding aryl hydroxy compounds with dicyclohexylcarbodiimide in the presence of a suitable base, for example pyridine or triethylamine, in an inert solvent. As a solvent, methylene chloride, ethylene chloride, chloroform, ethyl acetate, tetrahydrofuran, preferably chloroform, are suitable. The reaction is performed at temperatures between −30° C. and +50° C., preferably at +10° C.

The carbacyclin derivatives of general formula I with $R_1$ representing a carboxyl group can be converted, with suitable amounts of the corresponding inorganic base, with neutralization, into salts. For example, by dissolving the corresponding PG acids in water which contains the stoichiometric amount of the base, the solid inorganic salt if obtained after evaporation of the water or after addition of a water-miscible solvent, for example, alcohol or acetone.

Production of the amine salts occurs in the usual way. In addition, the PG acid is dissolved, for example, in a suitable solvent such as ethanol, acetone, diethyl ether or benzene and at least the stoichiometric amount of the amine of this solution is added. In doing so the salt usually precipitates in solid form or is isolated in the usual way after evaporation of the solvent.

The functional modification of the free OH group occurs according to methods known to a man of the art.

To introduce the ether protection group the reaction is performed with, for example, dihydropyran in methylene chloride or chloroform while using an acidic condensing agent, for example p-toluenesulfonic acid. An excess of dihydropyran is used, preferably 4 to 10 times the amount theoretically needed. The reaction is normally finished in 15 to 30 minutes at 0° C. -30° C.

The introduction of the acyl protection groups occurs by reacting a compound of general formula I in a way known in the art with a carboxylic acid derivative, such as acid chloride, acid anhydride, among others.

The release of a functionally modified OH group to the compounds of general formula I occurs according to known methods. For example, the cleavage of ether protection groups is performed in an aqueous solution of an organic acid, such as acetic acid, propionic acid, among others, or in an aqueous solution of an inorganic acid, such as hydrochloric acid. To improve the solubility, an water-miscible inert organic solvent is suitably added. Suitable organic solvents are, for example, alcohols such as methanol and ethanol, and ethers, such as dimethoxyethane, dioxane and tetrahydrofuran. Tetrahydrofuran is preferably used. The cleavage is preferably performed at temperatures between 20° C. and 80° C.

The cleavage of the silyl ether protection group is performed, for example, with tetrabutylammonium fluoride Tetrahydrofuran, diethyl ether, dioxane, and methylene chloride, for example, are suitable as solvents. The cleavage is performed preferably at temperatures between 0° C. and 80° C.

Saponification of the acyl groups is performed, for example, with alkali or alkaline-earth carbonates or hydroxides in an alcohol or the aqueous solution of an alcohol. As alcohols, aliphatic alcohols are suitable, such as methanol, ethanol, butanol, etc., preferably methanol As alkali carbonates and hydroxides there can be mentioned potassium and sodium salts, but the potassium salts are preferred. As alkaline-earth carbonates and hydroxides, calcium carbonate, calcium hydroxide and barium carbonate are, for example, suitable. The reaction takes place at −10° C. to 70° C., preferably at 25° C.

The introduction of the amide group $CONHR_3$ for $R_1$ occurs according to methods known to a man of the art. Carboxylic acids of general formula I ($R_2=H$) are first converted, in the presence of a tertiary amine such as triethylamine, with chloroformic acid isobutyl ester, into the mixed anhydride. The reaction of the mixed anhydride with the alkali salt of the corresponding amide or with ammonia ($R_3=H$) occurs in an inert solvent or solvent mixture, such as tetrahydrofuran, dimethoxyethane, dimethylformamide, and hexamethylphosphoric acid triamide at temperatures between −30° C. and +60° C., preferably at 0° C. to 30° C.

A further possibility for the introduction of the amide group $CONHR_3$ for $R_1$ consists in reacting a 1-carboxylic acid of general formula I ($R_2=H$), in which free hydroxy groups are protected intermediately, with compounds of general formula X $$O=C=N-R_3 \qquad (X),$$

in which $R_3$ has the above-mentioned meaning.

The reaction of the compound of general formula I ($R_1=COOH$) with an isocyanate of general formula VIII occurs optionally with the addition of a tertiary amine, such as triethylamine or pyridine. The reaction can occur without solvent or in an inert solvent, preferably acetonitrile, tetrahydrofuran, acetone, dimethylacetamide, methylene chloride, diethyl ether., toluene, at temperatures between −80° C. to 100° C., preferably at 0° C. to 30° C.

If the starting product contains OH groups in the prostane radical, these OH groups are also reacted. If, ultimately, end products containing free hydroxy groups in the prostane radical are desired, suitably a starting product is used in which these free hydroxy groups are intermediately protected by preferably easily cleavable ether or acyl radicals.

All remaining compounds of formula I can be produced according to processes described in laid-open specifications DE-OS 28 45 770, 3237 200, 33 22 893 and 34 05 181.

The carbacyclins of formula I, in which $R_9$ stands for the radical $-(CH_2)_m-R_6$ or $-(CH_2)_{m-o}-[Z_1-(CH_2)_{m-p}]_x-[Z_2-CH_2)_{m-q}]_y-R_6$ with $R_6$ as $NH_2$, $NHCH_3$, OH, COOH, or SH group, can be bonded very well without great loss of biological activity to polymer carriers. The new carbacyclins prevent the formation of platelet aggregations on the surface of these polymer carriers, such as vascular prosthetic devices or artificial heart valves. After chemical bonding to proteins, the compounds of formula I are suitable for the preparation of antibodies to prostacyclins of general formula I.

The compounds of this invention are furthermore suitable for therapy of diseases of the cardiovascular system, the stomach, the pancreas, the liver and the kidneys. They cause blood pressure reduction and bronchodilation. They are additionally suitable for the inhibition of platelet aggregation. Consequently, the new carbacyclin derivatives of formula I represent valuable pharmaceutical active ingredients. Furthermore, compared with corresponding prostaglandins and prostacyclins, they exhibit higher specificity and above all a substantially longer effectiveness in the same activity spectrum. Compared to $PGI_2$, they are distinguished by higher stability. The high tissue specificity of the new carbacyclins is shown with the study of smooth muscle organs, such as the guinea pig ileum or the isolated rabbit trachea, where a considerably lesser stimulation can be observed than with the application of natural prostaglandins of the E, A or F type.

The new carbacyclin analogues possess qualities typical for prostacyclins, such as reduction of the peripheral arterial and coronary vascular resistance, inhibition of platelet aggregation and dissolution of platelet clots, myocardial cytoprotection, reduction of the systemic blood pressure without at the same time reducing cardiac output and coronary blood circulation; treatment of stroke, prevention and therapy for coronary heart diseases, coronary thrombosis, cardiac infarction, peripheral arterial diseases, arteriosclerosis and thrombosis, prevention and therapy of ischemic attacks of the central nervous system, shock therapy, inhibition of bronchoconstriction, inhibition of stomach acid secretion and cytoprotection of the stomach and intestinal mucous membrane; cytoprotection in the liver, pancreas and kidney, antiallergic qualities, reduction of pulmonary vascular resistance and pulmonary blood pressure, stimulation of kidney blood circulation, use instead of heparin or as an adjunct in dialysis or blood filtration, storage of blood plasma supplies, especially of blood platelet supplies, inhibition of labor pains, treatment of pregnancy toxicosis, elevation of cerebral blood circulation, treatment of asthma, etc. In addition, the new carbacyclin analogues possess antiproliferative qualities. The new carbacyclins can also be used in combination, for example, with beta blockers or diuretics.

The new carbacyclins are furthermore distinguished by the suppression of rejection reactions and by its antimetastatic effect. With them, Botallo's duct (before operations) is kept open. They are further suitable for diarrhea treatment and to improve bowel movement.

The dose of the compounds is 1–1500 micrograms/kg/day, if they are administered to human patients. The unit dose for the pharmaceutically acceptable vehicles is 0.01–100 mg.

With intravenous injection in awake, hypertonic rats in doses of 5, 20 and 100 micrograms/kg body weight, the compounds according to the invention exhibit stronger blood pressure reduction and longer lasting effects than $PGE_2$ and $PGA_2$ without causing, as with $PGE_2$, diarrhea, or as with $PGA_2$, cardiac arrhythmias.

With intravenous injection in anesthetized rabbits, the compounds according to the invention exhibit, compared to $PGE_2$ and $PGA_2$, stronger and considerably longer lasting blood pressure reduction, without influencing other smooth muscle organs or organ functions.

For parenteral administration, sterile, injectable, aqueous or oily solutions are used. For oral application, tablets, dragees or capsules are suitable, for example.

The invention thus relates also to drugs based on compounds of general formula I and usual auxiliary agents and carriers.

The active ingredients according to the invention should function in conjunction with the usual auxiliary agents known in galenicals, such as for the production of blood pressure reduction agents.

The unit dose range for the ampoule is 0.1–0.5 mg, for tablets 0.1–1 mg.

EXAMPLE 1

5-(E)-{7-hydroxy-6-[(E)-3-hydroxy-4-methyl-oct-1-en-6-inyl]9-[6-amino-hexyl]-bicyclo[3.3.0]octan-3-yliden}pentaic acid 221 mg (0.5 mmol) of 7alpha-tetrahydropyran-2-yloxy)6beta-[(E)-4-methyl-3-(tetrahydropyran-2-yl-oxy)-oct-1-en-6-inyl]-bicyclo-[3.3.0]-oct-1-en-3-one and 12 mg of $Cu(OAc)_2 \cdot H_2O$ in 6 ml of absolute tetrahydroduran were mixed slowly at −15° C. with a Grignard reagent, prepared from 670 mg (2 mmol) of 2,2,5,5-tetramethyl-1-aza-2,5-disilacyclopentane-1 hexyl bromide and 103 mg of magnesium chips in 2 ml of absolute ether, until a pitch black color was achieved after several color changes.

After working up with $NH_4Cl$, the raw product was subsequently silylated according to the following formula for the starting material and the raw product, which according to TLC still contained 13% of the starting material, was subjected to a Wittig reaction with 10 equivalent of (4 carboxybutyl)triphenylphosphonium bromide/potassium tert-butylate in dimethyl sulfoxide-tetrahydrofuran =2:1. After 3 hours of stirring at 30° C., it was mixed with ice water, carefully neutralized with citric acid and extracted with ether. After chromatography on silica gel, pure 5-E-isomer was obtained, which yielded the desired 5-E end product after cleavage of the protection group with AcOH-$H_2O$-THF.

IR (oil film) 3400-3000 cm$^{-1}$ (NH$_2$ and OH) 1710-1600 cm$^{-1}$ (acid carbonyl and carboxylate)

2,2,5,5-tetramethyl-aza-2,5-disilacyclopentane-1-hexyl bromide was prepared as follows:

10 g (38.3 mmol) of 6-bromine-1-hexylamine hydrobromide and 8.25 g (38.3 mmol) of 1,2-bis(chlorodimethylsilyl)ethane were stirred in the presence of 15.9 ml (115 mmol) of triethylamine in 115 ml of methylene chloride for 3 hours at 24°, and triethylamine hydrochloride precipitated. After suctioning of the triethylamine hydrochloride and rewashing with methylene chloride, evaporation took place and the residue was absorbed in 50 ml of dry hexane, while the remaining triethylamine hydrochloride precipitated and was filtered off. After evaporation, about 11.52 g (93.3%) was obtained, which was distilled at 92°-102°/0.05 mm. The distillate is, like the raw product, slightly cloudy.

EXAMPLE 2

5-(E)-{7-(tetrahydropyran-2-yl-oxy)-6-[(E)-b 4-methyl-3-(tetrahydropyran-2-yl-oxy)-oct-1-en-6-inyl]-9-[5-hydroxy-pentyl]-bicyclo-]3.3.0]-octan-3-yliden}-pentaic acid To 740 mg (1.67 mmol) of 7 alpha-tetrahydropyran-2-yl-oxy)-6 beta-[(E)-4-methyl-3-(tetrahydropyran-2-yl-oxy)-oct-1-en-6-inyl]bicyclo[3.3.0]oct-1-en-3-one and 40.2 mg of Cu(OAc)$_2$. H$_2$O in 20 ml of absolute tetrahydrofuran was instilled in 10 minutes at −150°, a Grignard solution produced from 3.949 g of 5-tert-butyldimethylsilyloxypentylbromide and 689 mg of magnesium chips in 15 ml of absolute ether until a pitch black color occurred. After working up, the raw product was chromatographed on a column of about 150 g of SiO$_2$ in hexane-ether and 932 mg=86.4% pure bicyclic ketone was obtained. This 932 mg (1.445 mmol) was reacted analogously to Example 1 with excess (4-carboxybutyl)-triphenylphosphonium bromide and after working up the isomeric compounds were separated by chromatography in hexane-ether on 150 g of fine silica gel, and pure (e)-stereoisomer was obtained. By treatment with a tetrabutylammonium fluoride solution in THF, the tert-butyldimethylsilyl protection group saponified on the C-9 of the bicyclooctane skeleton selectively and the title compound formed. The reaction with acetic acid-H$_2$O -THF/80° then leads to the free carbacyclin derivative 5(E){(7-hydroxy-6[(E)-4-methyl-3-hydroxy-oct-1-en-6-inyl]-9[5-hydroxyl-pentyl]-bicyclo [3.3.0]-octan-3-yliden}-pentaic acid.

IR (oil film) 3300-3000 cm$^{-1}$ (OH).1740-1710 cm$^{-1}$ (acid carbonyl/wide/).

5-tert-butyldimethylsilyloxy-pentyl bromide was prepared as follows: 10.45 g (50 mmol) of 5-bromovaleric acid ethyl ester was reduced at 0° with 1.043 g of LiAlH$_4$ in 100 ml of absolute tetrahydrofuran, worked up with ice water, 2 N H$_2$SO$_4$ and chromatographed with pentane, 20% ether on a column with 275 g of silica gel, and 5.88 g of 5-bromopentyl alcohol was obtained.

7.01 g (42 mmol) of 5-bromopentyl alcohol was stirred in 20 ml of DMF with 3.571 g of imidazole and 7.906 g (52.5 mmol) of tert-butyldimethylsilyl chloride for 2 hours at 24°, ice water added and extracted with hexane/ether 1:1, and 12.58 g of raw product was obtained, which yielded 8.93 g (75%) of the title compound in pentane after chromatography on silica gel.

The following is the specification of U.S. Ser. No. 864,345, filed on May 12, 1986.

The invention relates to novel carbacyclin derivatives, processes for their preparation, as well as use thereof as medicinal agents: U.S. Pat. No. 4,420,632 discloses 9-alkylated carbacyclin derivatives exhibiting antithrombotic, antisecretory and bronchodilating properties. They furthermore act as thrombocyte aggregation inhibitors.

It has been found that, by substitution of the methylene group in the 3-position of these carbacyclins by oxygen, or by chain extension in the 9-position, biologically active derivatives are obtained exhibiting longer-lasting effectiveness, greater selectivity, and improved efficacy. The derivatives with lengthening of the chain in the 9-position can be bound to polymeric substrates with an only minor loss of biological activity. The compounds of this invention have bronchodilatory effects and are suitable for inhibition of thrombocyte aggregation, for lowering blood pressure via vasodilation, and for inhibition of gastric acid secretion.

The invention relates to carbacyclin derivatives of general Formula I

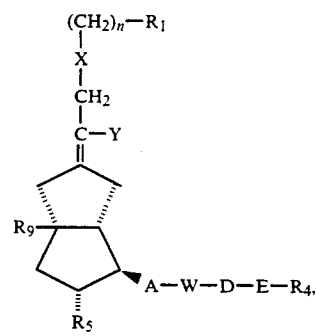

wherein
n is 1 or 3
R$_1$ is the residue

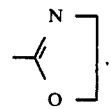

the residue

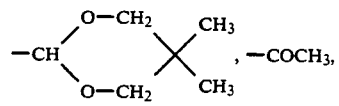

the residue COOR$_2$ wherein R$_2$ can mean hydrogen or alkyl of 1-10 carbon atoms optionally substituted by halogen, phenyl, C$_1$-C$_4$-alkoxy or C$_1$-C$_4$-dialkylamino; cycloalkyl, aryl, or a heterocyclic residue, or is the residue CONHR$_3$ with R$_3$ meaning hydrogen or an alkanoyl or alkanesulfonyl residue of respectively 1-10 carbon atoms, R$_9$ is an alkyl group of 1-10 carbon atoms or the group —C≡C—(CH$_2$)$_m$—R$_6$ wherein
m is 1 to 16 and
R$_6$ is hydrogen, hydroxy, amino or trimethylsilyl,
X is an oxygen atom or, if R$_9$ means an alkyl group of 5-10 carbon atoms, a methylene group,
Y is hydrogen or fluorine, A is a —CH₂—CH₂—, trans—CH=CH— or —C≡C—group, W is a free or functionally modified hydroxymethylene group or a free or functionally modified

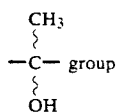

group wherein the OH-group can be in the α- or β-position,

D is the group

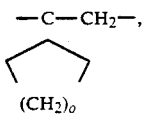

a straight-chain, saturated alkylene group of 1-5 carbon atoms, a branched saturated or a straight-chain or branched unsaturated alkylene group of 2-5 carbon atoms which latter can be optionally substituted by fluorine atoms, o is 1, 2 or 3, E is a direct bond, a —C≡C—group, or a —CH=C-R₇—group wherein R₇ is a hydrogen atom, an alkyl group of 1-5 carbon atoms, or halogen, R₄ is an alkyl group of 1-10 carbon atoms, a cycloalkyl group of 3-10 carbon atoms, or an optionally substituted aryl group of 6-10 carbon atoms, or a heterocyclic group, and R₅ is a free or functionally modified hydroxy group, and if R₂ means a hydrogen atom, the salts thereof with physiologically compatible bases.

The compounds of Formula I' represent (5E)- as well as (5Z)-isomers.

Alkyl groups R₂ can be straight- or branched-chain alkyl groups of 1-10 carbon atoms, such as, for example, methyl, ethyl, propyl, isopropyl, butyl, isobutyl, tert-butyl, pentyl, isopentyl, neopentyl, heptyl, hexyl, decyl.

The alkyl groups R₂ can optionally be mono- to polysubstituted by halogen atoms, C₁-C₄-alkoxy groups, phenyl, and di-C₁-C₄-alkylamines. Alkyl groups which are monosubstituted are preferred.

Examples for substituents are fluorine, chlorine or bromine atoms, phenyl, dimethylamino, diethylamino, methoxy, ethoxy.

Preferred alkyl groups R₂ are those of 1-4 carbon atoms, such as, for example, methyl, ethyl, propyl, dimethylaminopropyl, isobutyl, butyl.

Suitable aryl groups R₂ are substituted as well as unsubstituted aryl groups, such as, for example, phenyl, 1-naphthyl and 2-naphthyl, each of which can be substituted by 1-3 halogen atoms, a phenyl group, 1-3 alkyl groups of respectively 1-4 carbon atoms, a chloromethyl, fluoromethyl, trifluoromethyl, carboxy, hydroxy, or alkoxy group of 1-4 carbon atoms.

The substituents in the 3- and 4- positions on the phenyl ring are preferred, for example by fluorine, chlorine, alkoxy or trifluoromethyl, or in the 4-position by hydroxy.

The cycloalkyl group R₂ can contain in the ring 4-10, preferably 5 and 6 carbon atoms. The rings can be substituted by alkyl groups of 1-4 carbon atoms. Examples that can be cited are cyclopentyl, cyclohexyl, methylcyclohexyl and adamantyl.

Suitable heterocyclic groups R₂ can be 5- and 6-membered heterocycles containing at least one hetero atom, preferably nitrogen, oxygen or sulfur. Examples are 2-furyl, 3-furyl, 2-thienyl, 3-thienyl, 2-pyridyl, 3-pyridyl, 4-pyridyl, and others.

Suitable as the acid residue R₃ are physiologically compatible acid residues. Preferred acids are organic carboxylic acids and sulfonic acids of 1-15 carbon atoms pertaining to the aliphatic, cycloaliphatic, aromatic, aromatic-aliphatic, and heterocyclic series. These acids can be saturated, unsaturated and/or polybasic and/or substituted in the usual way. Examples for the substituents are C₁-C₄-alkyl, hydroxy, C₁-C₄-alkoxy, oxo or amino groups, or halogen atoms (F, Cl, Br).

The following carboxylic acids are cited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid. Especially preferred acyl residues are considered to be those of up to 10 carbon atoms. Examples for sulfonic acids are methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino- and morpholinosulfonic acid, sulfonic acids of up to 10 carbon atoms being especially preferred.

The hydroxy groups R₅ and those in W can be functionally modified, for example by etherification or esterification, wherein the free or modified hydroxy groups in W can be in the α- or β-position, free hydroxy groups being preferred.

Suitable as the ether and acyl residues are those known to persons skilled in the art. Ether residues that can be readily split off are preferred, such as, for example the tetrahydropyranyl, tetrahydrofuranyl, α-ethoxyethyl, trimethylsilyl, dimethyl-tert-butylsilyl and tri-p-benzylsilyl residue. The acyl residues are the same as recited for R₃; worth mentioning by name, for example, are acetyl, propionyl, butyryl, benzoyl.

Suitable as the alkyl group R₄ are straight- and branched-chain, saturated and unsaturated alkyl residues, preferably saturated ones, of 1-10, especially 1-4 carbon atoms.

Examples that can be cited are methyl, ethyl, propyl, butyl, isobutyl, tert-butyl, pentyl, hexyl, heptyl, octyl, butenyl, isobutenyl, propenyl, pentenyl, hexenyl, or carboxy-group-substituted benzoic acids, nicotinic acid, isonicotinic acid, furan-2-carboxylic acid, cyclopentyl-propionic acid. Especially preferred acyl residues are those of up to 10

The cycloalkyl group $R_4$ can contain in the ring 3-10, preferably 5 and 6 carbon atoms. The rings can be substituted by alkyl groups of 1-4 carbon atoms. Examples are cyclopentyl, cyclohexyl, methylcyclohexyl and adamantyl.

Suitable substituted or unsubstituted aryl groups $R_4$ are, for example: phenyl, 1-naphthyl and 2-naphthyl, each of which can be substituted by 1-3 halogen atoms, a phenyl group, 1-3 alkyl groups of 1-4 carbon atoms each, a chloromethyl, fluoromethyl, trifluoromethyl, carboxy, $C_1$-$C_4$-alkoxy or hydroxy group. The substitution in the 3- and 4-positions on the phenyl ring is preferred, for example by fluorine, chlorine, $C_1$-$C_4$-alkoxy or trifluoromethyl, or in the 4-position by hydroxy.

Suitable heterocyclic groups $R_4$ are 5- and 6-membered heterocycles containing at least one hetero atom, preferably nitrogen, oxygen or sulfur. Examples that can be cited are 2-furyl, 2-thienyl, 2-pyridyl, 3-pyridyl, 4-pyridyl, 3-furyl, 3-thienyl, and others.

The alkylene group D can be straight-chain or branched-chain, saturated and unsaturated alkylene residues, preferably saturated ones of up to 5 carbon atoms which can optionally be substituted by fluorine atoms, 1,2-methylene, 1,1-trimethylene, 1,1-tetramethylene or 1,1-pentamethylene. Examples are: methylene, fluoromethylene, ethylene, 1,2-propylene, ethylethylene, trimethylene, tetramethylene, pentamethylene, 1-methyltetramethylene, 1-methyltrimethylene, 1,1-trimethylenethylene, 1,1-tetramethylenethylene.

Especially preferred compounds of this invention are those wherein E is —C≡C— or —CH=CR₇— with $R_7$ meaning an alkyl group of 1-5 carbon atoms.

Suitable alkyl groups $R_7$ of 1-5 carbon atoms are the groups already cited for the alkyl group $R_4$.

In the meaning of halogen, $R_7$ is fluorine, chlorine and bromine.

Suitable as the alkyl group $R_9$ of 1-10 carbon atoms are the groups recited above for $R_4$.

Among the residues —C≡C—$(CH_2)_m$—$R_6$ for $R_9$, residues with m=1-8 are preferred.

Inorganic and organic bases are suitable for salt formation with the free acids ($R_2$=H), as they are known to persons skilled in the art for the formation of physiologically compatible salts. Examples are: alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention relates furthermore to a process for the preparation of the carbacyclins of general Formula I' according to this invention wherein X means an oxygen atom, characterized by conventionally etherifying, in the presence of a base, a compound of general Formula II'

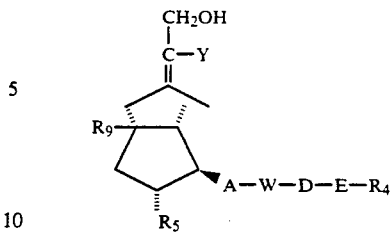

wherein $R_4$, $R_5$, $R_9$, A, W, Y, D and E have the meanings given above, optionally after blockage of free hydroxy groups present, with a haloalkanoic acid derivative of general Formula III'

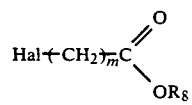

wherein n is 1 or 3; Hal is a chlorine or bromine atom; and $R_8$ is an alkyl residue of 1-4 carbon atoms or an alkali metal,
and optionally subsequently, in any desired sequence, separating isomers and/or liberating blocked hydroxy groups and/or esterifying, etherifying free hydroxy groups and/or esterifying a free carboxy group and/or saponifying an esterified carboxy group, or converting a carboxy group into an amide or, with a physiologically compatible base, into a salt.

Reaction of the compound of general Formula II' with a haloalkanoic acid derivative of general Formula III' is conducted at temperatures of 0° C. to 100° C., preferably 10°-80° C., in an aprotic solvent or solvent mixture, for example dimethyl sulfoxide, dimethylformamide, tetrahydrofuran, etc. Suitable bases are the bases known to one skilled in the art for etherifications, e.g. sodium hydride, potassium tertbutylate, butyllithium, etc.

Saponification of the carbacyclin esters is performed according to the methods known to persons skilled in the art, such as, for example, with alkaline catalysts.

The ester group $COOR_2$ wherein $R_2$ is an alkyl group of 1-10 carbon atoms is introduced for $R_1$ in accordance with the methods known to one skilled in the art. The carboxy compounds are, for example, conventionally reacted with diazo hydrocarbons. Esterification with diazo hydrocarbons takes place, for example, by mixing a solution of the diazo hydrocarbon in an inert solvent, preferably in diethyl ether, with the carboxy compound in the same or in another inert solvent, e.g. methylene chloride. After the reaction is finished within 1-30 minutes, the solvent is removed and the ester purified as usual. Diazo alkanes are either known or can be prepared according to known methods [Org. Reactions 8: 389-394 (1954)].

Introduction of the ester group $COOR_2$ for $R_1$ wherein $R_2$ is a substituted or unsubstituted aryl group takes place by means of methods known to those skilled in the art. The carboxy compounds are reacted, for example, with the corresponding aryl hydroxy compounds with dicyclohexylcarbodiimide in the presence of a suitable base, e.g. pyridine or triethylamine, in an inert solvent. Suitable solvents are methylene chloride, ethylene chloride, chloroform, ethyl acetate, tetrahydrofuran, preferably chloroform. The reaction is conducted at temperatures of between −30° C. and +50° C., preferably at +10° C.

The carbacyclin derivatives of general Formula I wherein $R_1$ means a carboxy group can be converted into salts with suitable amounts of the corresponding inorganic bases under neutralization. For example, by dissolving the corresponding PG acids in water containing the stoichiometric quantity of the base, the solid inorganic salt is obtained after evaporation of the water or after addition of a water-miscible solvent, e.g. alcohol or acetone.

The amine salts are produced in the usual way. For this purpose, the PG acid is, for example, dissolved in a suitable solvent, such as ethanol, acetone, diethyl ether, or benzene, and at least the stoichiometric amount of the amine is added to this solution. During this process, the salt is ordinarily obtained in the solid form or is conventionally isolated after evaporation of the solvent.

Functional modification of the free OH-groups takes place according to the methods known to persons skilled in the art. For introduction of the ether blocking groups, for example, the reaction is executed with dihydropyran in methylene chloride or chloroform with the use of an acidic condensation agent, e.g. p-toluenesulfonic acid. Dihydropyran is added in excess, preferably in four to ten times the amount required theoretically. The reaction is normally concluded at 0° C. to 30° C. after 15–30 minutes.

The acyl blocking groups are introduced by reacting a compound of general Formula I in a manner known per se with a carboxylic acid derivative, e.g. an acid chloride, acid anhydride, and others.

Liberation of a functionally modified OH-group to obtain the compounds of general Formula I takes place according to known methods. For example, ether blocking groups are split off in an aqueous solution of an organic acid, e.g. acetic acid, propionic acid, and others, or in an aqueous solution of an inorganic acid, e.g. hydrochloric acid. For improving solubility, a water-miscible, inert organic solvent is suitably added. Organic solvents that can be used are, for example, alcohols, such as methanol and ethanol, and ethers, such as dimethoxyethane, dioxane and tetrahydrofuran. Tetrahydrofuran is utilized with preference. The splitting-off step is preferably performed at temperatures of between 20° C. and 80° C.

The silyl ether blocking groups are split off, for example, with tetrabutylammonium fluoride. Examples of suitable solvents are tetrahydrofuran, diethyl ether, dioxane, methylene chloride, etc. The splitting-off step is preferably conducted at temperatures of between 0° C. and 80° C.

Saponification of the acyl groups takes place, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Alkali carbonates and hydroxides that can be mentioned are potassium and sodium salts, but the potassium salts are preferred. Examples of suitable alkaline earth carbonates and hydroxides are calcium carbonate, calcium hydroxide and barium carbonate. The reaction takes place at −10° C. to 70° C., preferably at 25° C.

Introduction of the amide group $CONHR_3$ for $R_1$ is performed according to methods known to those skilled in the art. The carboxylic acids of general Formula I' ($R_2$=H) are first converted into the mixed anhydride with the isobutyl ester of chloroformic acid in the presence of a tertiary amine, e.g. triethylamine. The reaction of the mixed anhydride with the alkali salt of the corresponding amide or with ammonia ($R_3$=H) is conducted in an inert solvent or solvent mixture, such as, for example, tetrahydrofuran, dimethoxyethane, dimethylformamide, hexamethylphosphoric triamide, at temperatures of between −30° C. and +60° C., preferably at 0°–30° C.

Another possibility for introducing the amide group $CONHR_3$ for $R_1$ resides in reacting a 1-carboxylic acid of general Formula I' ($R_2$=H, wherein free hydroxy groups are intermediately protected, with compounds of general Formula IV'

   $O=C=N-R_3$   IV' wherein $R_3$ has the meanings given above.

Reaction of the compound of general Formula I' ($R_1$=COOH) with an isocyanate of general Formula IV' optionally takes place with addition of a tertiary amine, such as, for example, triethylamine or pyridine. The reaction can be performed without solvents or in an inert solvent, preferably acetonitrile, tetrahydrofuran, acetone, dimethylacetamide, methylene chloride, diethyl ether, toluene, at temperatures of between −80° C. to 100° C., preferably at 0°–30° C.

If the starting compound contains OH-groups in the prostane residue, then these OH-groups are likewise reacted. If, in the final analysis, end products are desired which contain free hydroxy groups in the prostane residue, starting compounds are suitably utilized wherein these are intermediately blocked by preferably readily cleavable ether or acyl residues.

All the remaining compounds of Formula I' can be prepared according to processes described in Laid-Open Applications DOS's 2,845,770; 3,237,200; 3,322,893; and 3,405,181. In case the residue $R_9$ is an alkynyl group, the residue $R_9$ can be introduced according to the method disclosed by R. T. Hansen et al., JACS 100:2244 (1978).

The compounds of this invention are especially suitable for therapy of diseases of the cardiovascular system, the stomach, the pancreas, the liver, and the kidney. They have hypotensive and bronchodilatory effects. They are furthermore suited for inhibiting thrombocyte aggregation. Consequently, the novel carbacyclin derivatives of Formula I represent valuable pharmaceutically active agents. Moreover, they exhibit, with a similar spectrum of activity, a higher specificity and, above all, a substantially longer lasting efficacy as compared with corresponding prostaglandins and prostacyclins. As compared with $PGI_2$, they are distinguished by higher stability. The high tissue specificity of the novel carbacyclins is demonstrated in a study on smooth muscle organs, such as, for example, on the guinea pig ileum or on the isolated rabbit trachea where a substantially lower stimulation can be observed than in the administration of natural prostaglandins of the E-, A- or F-type.

The novel carbacyclin analogs exhibit the properties typical for prostacyclins, such as, for example, lowering of peripheral arterial and coronary vascular resistance, inhibition of thrombocyte aggregation and dissolution of platelet thrombi, myocardial cytoprotection, lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion and cytoprotection of gastric and intestinal mucosa; cytoprotection in liver, pancreas, and kidney, antiallergic properties, lowering of pulmonary vascular resistance and pulmonary blood pressure, promotion of renal blood flow, utilization in place of heparin or as adjuvant in dialysis or hemofiltration, preservation of stored blood plasma, especially stored blood platelets, inhibition of labor, treatment of gestational toxicosis, enhancement of cerebral blood flow, treatment of asthma, etc. The novel carbacyclin analogs furthermore exhibit antiproliferative properties. The novel carbacyclins can additionally be utilized in combination, for example, with $\beta$-blockers or diuretics.

The novel carbacyclins are furthermore also distinguished by suppressing rejection reactions and by their antimetastatic activity. They act to keep Botallo's duct open (before surgery). They are furthermore suitable for treatment of diarrhea and for improving bowel action.

The carbacyclins of Formula I' wherein $R_9$ is the residue —C≡C—$(CH_2)_m$—$R_6$ wherein $R_6$ is an OH- or $NH_2$-group can be bound very readily and without appreciable loss of biological activity to polymeric substrates. The novel carbacyclins prevent formation of thrombocyte aggregates on the surface of these polymeric substrates, such as, for example, artificial blood vessels or artificial heart valves.

Dosage of the compounds is 1–1,500 μg/kg/day if administered to human patients. The unit dosage for the pharmaceutically acceptable carrier is 0.01–100 mg.

With intravenous injection administered to nonanesthetized, hypertonic rats in doses of 5, 20, and 100 μg/kg body weight, the compounds of this invention exhibit a stronger hypotensive effect and a more prolonged duration of efficacy than $PGE_2$ and $PGA_2$ without triggering diarrhea, as does $PGE_2$, or cardiac arrhythmias, as does $PGA_2$.

Upon intravenous injection administered to anesthetized rabbits, the compounds of this invention show, as compared with $PGE_2$ and $PGA_2$, a stronger and also considerably prolonged hypotensive activity without affecting other smooth muscle organs or organ functions.

Sterile, injectable, aqueous or oily solutions are used for parenteral administration. Suitable for oral administration are, for example, tablets, dragees or capsules.

The invention accordingly also concerns medicinal agents based on the compounds of general Formula I' and conventional auxiliary agents and excipients.

The active agents of this invention are to serve, in conjunction with the auxiliary ingredients known and customary in galenic pharmacy, for example for the preparation of hypotensors.

The unit dosage range for an ampoule is 0.1–0.5 mg, for tablets 0.1–1 mg.

EXAMPLE 1

1$\beta$-Methyl-7$\alpha$-(tetrahydropyran-2-yloxy)-6$\beta$-[3$\alpha$-(tetrahydropyran-2-yloxy)-4-methyl-6,7-tetradehydrotrans-1-octenyl]bicyclo[3.3.0]octan-3-one At $-5°$, 27 ml of a 1.6N methyllithium solution in ether is gently added dropwise under agitation within 15 minutes to a suspension of 4.28 g (22.5 mmol) of $Cu^II$ in 25 ml of absolute ether, and to this solution is gradually added dropwise 2.21 g (5 mmol( of 7$\alpha$-(tetrahydropyran-2-yloxy)-6$\beta$-[3$\alpha$-(tetrahydropyran-2-yloxy)-4-methyl-6,7-tetradehydrotrans-1-octenyl]bicyclo[3.3.0]oct-1-en-3-one (cf. DOS 3,142,733) in 20 ml of ether at $-25°$ during 15 minutes. After another hour of agitation at $-25°$ to $-30°$, the mixture is gently combined with 100 ml of $NH_4Cl$ solution and extracted with ether. After washing with saturated sodium chloride solution, drying, and evaporation, 2.37 g of a crude product is obtained which is chromatographed on a column of 120 g of silica gel. Elution with hexane-ether (7:3) yielded 1.54 g (67%) of the above-mentioned product.

EXAMPLE 4

3-Oxa-9$\beta$-methyl-16-methyl-18,19-tetradehydrocarbacyclin

The 5-ring ketone described in Example 3 is reacted, according to EP 55208, with the methyl ester of dimethoxyphosphonoacetic acid in the presence of potassium tert-butylate, then reduced with lithium aluminum hydride, and the E-configured alkyl alcohol is finally reacted with 2-chloro- or 2-bromoacetic acid salts or esters in the presence of bases with subsequent cleavage of the tetrahydropyranyl blocking group to 3-oxa-9$\beta$-methyl-16-methyl-18,19-tetrahydrocarbacyclin.

EXAMPLE 5

1-(2-Trimethylsilylethynyl)-7$\alpha$-(tetrahydrpyran-2-yloxy)-6$\beta$-[3 - tetrahydropyran-2-yloxy)-4-methyl-6,7-tetradehydrotrans-1-octenyl]bicyclo[3.3.0]octanone At $-35°$, 0.33 ml (2.34 mmol) of trimethylsilylacetylene in 5 ml of toluene is combined with 2.34 ml of 1-molar butyllithium solution in hexane and agitated for 15 minutes at $-35°$. Then, 2.34 ml of 1-molar diethylaluminum chloride solution in hexane is added thereto and the mixture is stirred for 2 hours at 0°.

In parallel thereto, 56 mg (0.22 mmol) of sublimed nickel acetylacetonate in 3 ml of toluene is combined at $-15°$ with 0.17 ml (0.21 mmol) of a 1.2-molar DIBAL-H solution in toluene. The black nickel solution is then added at $-15°$ to the above solution of 1-trimethylsilyl-2-diethylaluminum acetylene.

To this solution is added, at $-10°$, 440 mg (1 mmol) of 7$\alpha$-(tetrahydropyran-2-yloxy)-6$\beta$-3$\alpha$-(tetrahydropyran-2-yloxy)-4-methyl-6,7-tetradehydrotrans-1-octenyl)bicyclo[3.3.0]octen-1-en-3-one and the mixture is stirred for 90 minutes at $-10°$ whereafter it is diluted with ether and extracted by shaking with $NaH_2PO_4$ solution. After washing the organic phase with saturated NaCl solution, the mixture is dried ($Na_2SO_4$) and evaporated, thus obtaining 610 mg of a crude product. Chromatography with hexane-ether on silica gel yields 307 mg (57%) of pure product.

EXAMPLE 6

3-Oxa-9-ethynyl-16-methyl-18,19-tetradehydrocarbacyclin

After reaction of the 5-ring ketone obtained in Example 5 with the methyl ester of dimethoxyphosphonoacetic acid, lithium aluminum hydride reduction, as well as separation of the E-, Z-isomers, the E-isomer is made to react, as described, with 2-haloacetic acid salts or esters (cf. EP 55208) in the presence of bases. Subsequent splitting off of the THP groups with acetic acid-H₂O in THF, as well as removal of the trimethylsilyl blocking group from acetylene in the 9-position with AgNO₃/KCN yield the desired free carbacyclin.

We claim:

1. A carbacyclin derivative of formula I:

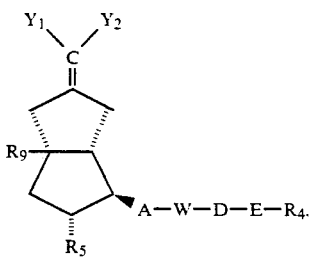

wherein $Y_1$ is the radical —$CH_2$—X—$(CH_2)_n$—$R_1$ or the radical

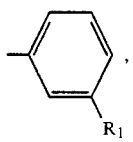

n is 1 or 3,
$R_1$ is the radical

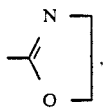

the radical

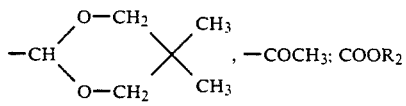

wherein $R_2$ is hydrogen; $C_1$-$C_{10}$-alkyl optionally substituted by halogen, phenyl, $C_1$-$C_4$-alkoxy or $C_1$-$C_4$-dialkyl amino; $C_4$-$C_{10}$-cycloalkyl; $C_6$-$C_{10}$-aryl optionally substituted by 1-3 halogen atoms, a phenyl group, 1-3 alkyl groups of 1-4 carbon atoms each or a chloromethyl, fluoromethyl, trifluoromethyl, carboxy, hydroxy, or alkoxy group of 1-4 carbon atoms; or a 5- or 6-membered heterocyclic ring containing at least one O, N or S atom; or the radical CONHR₃, wherein R₃ is hydrogen or an alkanoyl or alkane sulfonyl radical each with 1-10 C atoms, $R_9$ is the radical —$(CH_2)_{m-o}$—$[Z_1-(CH_2)_{m-p}]_x$—$[Z_2-(CH_2)_{m-q}]_y$—$R_6$, and $R_6$ must be separated at least by two atoms from the C-9 carbon atom of the carbacyclin bicyclic compound, m=2-20,
o, p, and q are less than or equal to 19,
x, y=0, 1, or 2,
$Z_1$ is a cis—CH=CH group, a trans—CH=CH group or a —C≡C group and each of these groups must be separated at least by a methylene group from the C-9 carbon atoms of the carbacyclin bicyclic compound, $Z_2$ is oxygen, sulfur, an NH or an N methyl group,
$R_6$ is amino, methylamino, carboxy or mercapto,
X is an oxygen atom or a methylene group,
$Y_2$ is hydrogen or fluorine,
A is a —$CH_2$—$CH_2$, trans—CH=CH or —C≡C group,
W is a free or functionally modified hydroxy methylene group or a free or functionally modified

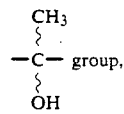

and the OH group can be in alpha or beta position,
D is the group

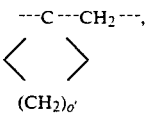

a straight-chain, saturated alkylene group with 1-5 C atoms, a branched, saturated or a straight-chain or branched unsaturated alkylene group with 2-5 C atoms, which latter optionally can be substituted by fluorine atoms, o' is 1, 2, or 3,
E is a direct bond, a —C≡C group or a —CH=CR₇ group wherein R₇ is a hydrogen atom, an alkyl group with 1-5 C atoms or halogen,
$R_4$ is an alkyl group with 1-10 C atoms, a cycloalkyl group of 3-10 atoms, or an aryl group of 6-10 C atoms optionally substituted by 1-3 halogen atoms, a phenyl group, 1-3 alkyl groups of 1-4 carbon atoms each, or a chloromethyl, fluoromethyl, trifluoromethyl, carboxy hydroxy, or alkoxy group of 1-4 carbon atoms, or a heterocyclic group as defined for R₂, and
$R_5$ is a free or functionally modified hydroxy group, or when $R_2$ is a hydrogen atom, a physiologically compatible salt thereof with a base.

2. A compound of claim 1, wherein $R_6$ is —$NH_2$.
3. A compound of claim 1, wherein $R_6$ is —$NHCH_3$.
4. A compound of claim 1, wherein $R_6$ is —SH.
5. A compound of claim 1, wherein $R_6$ is —COOH.
6. A compound of claim 1, wherein A is a —C≡C— group.
7. A pharmaceutical composition comprising an amount of a compound of claim 1 effective to inhibit thrombocyte aggregation and a pharmaceutically effective carrier.
8. A method of inhibiting thrombocyte aggregation in a patient comprising administering to the patient an effective amount of a compound of claim 1.
9. A carbacyclin derivative of formula I:

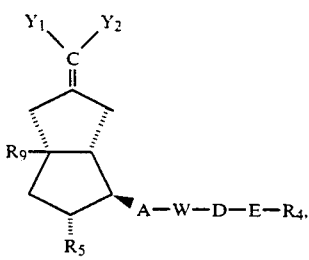 (I)

wherein

Y₁ is the radical —CH₂—X—(CH₂)ₙ—R₁ or the radical

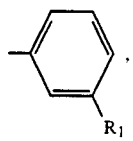, n is 1 or 3,
R₁ is the radical

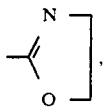

the radical

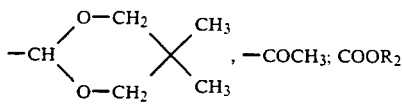

wherein R₂ is hydrogen or C₁-C₁₀-alkyl optionally substituted by halogen, phenyl, C₁-C₄-alkoxy or C₁-C₄-dialkyl amino; C₄-C₁₀-cycloalkyl; C₆-C₁₀-aryl optionally substituted by 1-3 halogen atoms, a phenyl group, 1-3 alkyl groups of 1-4 carbon atoms each or a chloromethyl, fluoromethyl, trifluoromethyl, carboxy, hydroxy, or alkoxy group of 1-4 carbon atoms; or a 5- or 6-membered heterocyclic ring containing at least one O, N or S atoms; or the radical CONHR₃, wherein R₃ is hydrogen or an alkanoyl or alkane sulfonyl radical each wit 1-10 C atoms, R₉ is the radical —(CH₂)ₘ₋ₒ—[Z₁—(CH₂)ₘ₋ₚ]ₓ—[Z₂—(CH₂)ₘ₋q]ᵧ—R₆, and R₆ must be separated at least by five atoms from the C-9 carbon atom of the carbacyclin bicyclic compound, m=2-20,
o, p, and q are less than or equal to 19,
x, y=0, 1 or 2,
Z₁ is a cis—CH=CH group, a trans—CH=CH group or a —C≡C group and each of these groups must be separated at least by a methylene group from the C-9 carbon atoms of the carbacyclin bicyclic compound, Z₂ is oxygen, sulfur, an NH or an N methyl group,
R₆ is hydroxy,
X is an oxygen atom or a methylene group,
Y₂ is hydrogen or fluorine,
A is a —CH₂—CH₂, trans—CH=CH or —C≡C group,
W is a free or functionally modified hydroxy methylene group or a free or functionally modified

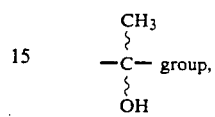 group, and the OH group can be in alpha or beta position,
D is the group

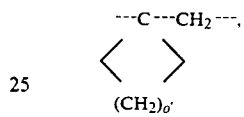

a straight-chain, saturated alkylene group with 1-5 C atoms, a branched, saturated or a straight-chain or branched unsaturated alkylene group with 2-5 C atoms, which latter can be optionally substituted by fluorine atoms, o' is 1, 2, or 3,
E is a direct bond, a —C≡C group or a —CH=CR₇ group, wherein R₇ stands for a hydrogen atom, an alkyl group with 1-5 C atoms or halogen,
R₄ is an alkyl group with 1-10 C atoms, a cycloalkyl group with 3-10 atoms or an aryl group of 6-10 carbon atoms optionally substituted by 1-3 halogen atoms, a phenyl group, 1-3 alkyl groups of 1-4 carbon atoms each, or a chloromethyl, fluoromethyl, carboxy, hydroxy, or alkoxy group of 1-4 carbon atoms, or a heterocyclic group as defined for R₂,
R₅ is a free or functionally modified hydroxy group, or when R₂ is a hydrogen atom, a physiologically compatible salt thereof with a base.

10. A pharmaceutical composition comprising an amount of a compound of claim 9 effective to inhibit thrombocyte aggregation and a pharmaceutically effective carrier.

11. A method of inhibiting thrombocyte aggregation in a patient comprising administering to the patient an effective amount of a compound of claim 10.

12. 5(E)-{7-hydroxy-6[(E)-4-methyl-3-hydroxy-oct-1-en-6-inyl]-9[5-hydroxyl-pentyl]-bicyclo[3.3.0]-octan-3-yliden}-pentaic acid, a compound of claim 9.

* * * * *

UNITED STATES PATENT AND TRADEMARK OFFICE
CERTIFICATE OF CORRECTION

PATENT NO. : 5,162,353

DATED : November 10, 1992

INVENTOR(S) : Helmut VORBRUEGGEN et al.

It is certified that error appears in the above-identified patent and that said Letters Patent is hereby corrected as shown below:

On the title page under item [75] Inventors:

Please add --Ulrich Klar--

Signed and Sealed this

Nineteenth Day of October, 1993

*Attest:*

BRUCE LEHMAN

*Attesting Officer*    *Commissioner of Patents and Trademarks*